United States Patent [19]

Healey

[11] 4,133,638
[45] Jan. 9, 1979

[54] METHOD OF STERILIZING POWDERS IN A FLUIDIZED BED

[75] Inventor: Dennis R. Healey, Loughborough, England

[73] Assignee: The Boots Company Limited, Nottingham, England

[21] Appl. No.: 742,162

[22] Filed: Nov. 15, 1976

[30] Foreign Application Priority Data

Nov. 14, 1975 [GB] United Kingdom ............... 46973/75

[51] Int. Cl.² .......................... A61L 1/00; A61L 13/00
[52] U.S. Cl. ......................................... 422/32; 422/37
[58] Field of Search ................... 21/58, DIG. 4, 91–93

[56] References Cited

U.S. PATENT DOCUMENTS

| | | | |
|---|---|---|---|
| 3,042,533 | 7/1962 | McConnell et al. | 21/58 |
| 3,088,179 | 5/1963 | Leuthner | 21/DIG. 4 |
| 3,341,280 | 9/1967 | Eolkin | 21/91 |
| 3,721,527 | 3/1973 | Lodige et al. | 21/93 |
| 3,897,210 | 7/1975 | Gruber et al. | 21/58 |
| 3,994,685 | 11/1976 | Lodige et al. | 21/93 |

Primary Examiner—Morris O. Wolk
Assistant Examiner—Bradley R. Garris
Attorney, Agent, or Firm—Lawrence Rosen; E. Janet Berry

[57] ABSTRACT

Powders, such as talc, can be sterilized by passing a sterilant containing gas through the powder while it is being stirred.

3 Claims, 1 Drawing Figure

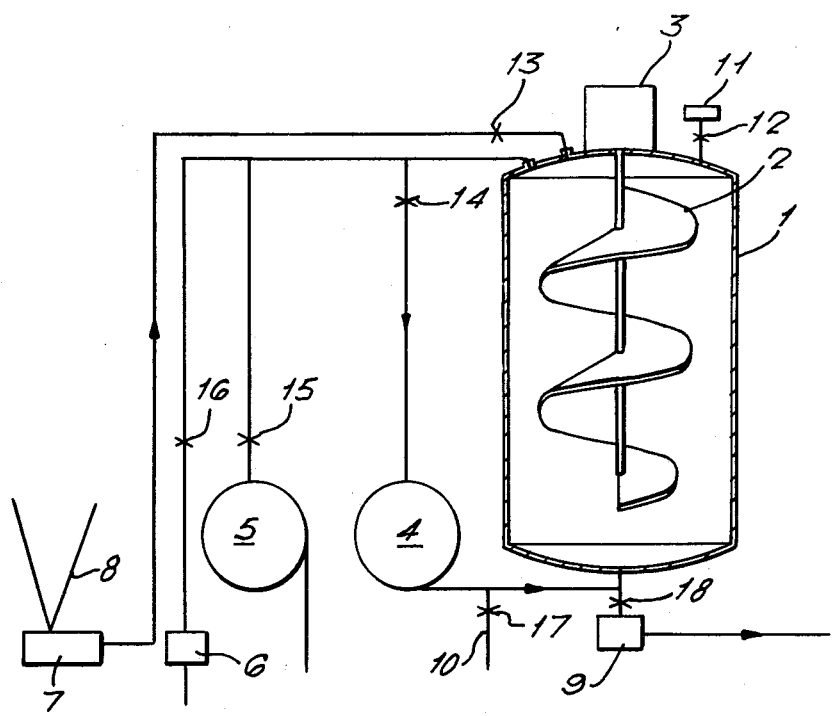

METHOD OF STERILIZING POWDERS IN A FLUIDIZED BED

This invention relates to the sterilization of powders.

It has been proposed in B.P. No. 1,147,640 to sterilize powders, such as talc, by fluidizing a bed of the powder, with a stream of gas which comprises a material which is toxic to the organisms in respect of which sterility is to be achieved. Fluidizing helps in obtaining an intimate contact between the powder and the sterilizing medium.

A commonly used sterilizing agent is ethylene oxide, but because of its inflammatory and explosive nature it is often mixed with a compound, usually a fluorinated hydrocarbon, to render it less dangerous. A typical mixture is that sold under the trade name "Sterethox" which is mixture of 12% by weight ethylene oxide and 88% by weight dichlorodifluoromethane.

Since talc approximately doubles its bulk on fluidizing with a gas or vapour, the sterilizing vessel can only be initially filled to about a third full and therefore to replace all the air a large amount of sterilizing gas is generally required, which is very expensive.

It would be advantageous if the sterilizing vessel could be almost filled with powder since this would reduce the amount of sterilizing gas to fill the vessel and also allow a much larger quantity of powder to be sterilized at any one time.

We have attempted to sterilize powder under these conditions in which the powder was stirred to ensure intimate contact between the powder and sterilizing gas. However, it was found that stirring failed to fluidize the talc and tended to compact it. Further a very high powered-motor was required to operate the stirrer.

We have now overcome the disadvantages by circulating gas through the powder at the same time as stirring.

Thus, according to the present invention, there is provided a method of sterilizing a powder which comprises passing a stream of gas or vapour, comprising a sterilant, through the powder whilst stirring the powder with a mechanical stirrer, the combination of the passage of the gas and the stirring being sufficient to maintain the powder in a fluidized state.

Preferably the vessel containing the powder is evacuated before introducing the sterilizing gas.

According to the invention there is also provided an apparatus suitable for sterilizing a powder which comprises a vessel for the powder, a mechanical stirrer within the vessel and means for circulating a stream of gas or vapour through the powder when contained in the vessel, the combination of the passage of gas and the action of the stirrer being such as to maintain the powder in the vessel in a fluidized state.

The invention is illustrated in the accompanying drawing which is a diagramatic representation of a typical apparatus according to the invention.

Referring to the drawing:

A sterilizing vessel 1 includes a stirrer 2 operated by motor 3. A blower 4 can blow vapour or gas through the sterilizing vessel. A vaccum pump 5 is provided to evacuate the vessel. A vaporizer 6 vaporizes liquid sterilant before it is introduced to the vessel. A pump transfers powder from a hopper 8 to the vessel 1. A second pump 9 transfers powder to storage vessels not shown. Air can be admitted to the vessel along line 10. Used sterilizing gas can be removed through vent 11. Valves 12, 13, 14, 15, 16, 17 and 18 are provided to control the lines entering and leaving the vessel 1.

In a typical operation to sterilize a batch of talc, powder from hopper 8 is pumped into the vessel until it is approximately three-quarters full. Air is then removed by the vacuum pump 5. Sterilant ("Sterethox") is then vaporized in the vaporizer 6 and the vapour passed into the vessel. The blower 4 then circulates the vapour in the direction of the arrows and the stirrer 2 is operated. The combination of the stirrer and the circulating vapour fluidizes the talc ensuring that all the particles are contacted with the vapour. This is continued until the powder reaches the required degree of sterility. The stirrer and circulation of the sterilant is stopped, the sterilant is vented through 11 and powder removed by pump 9 to a storage vessel.

In this way, talc is successfully sterilized by fluidization using less "Sterethox" than operating without a stirrer. Further the total energy requirements to blow the sterilizing gas through the powder and operate the stirrer is much less than if the fluidization is carried out using either of these methods alone.

I claim:

1. A method of sterilizing a powder in a sterilizing vessel which comprises passing a stream of gas or vapour, comprising a sterilant, through the powder whilst stirring the powder with a mechanical stirrer, circulating said sterilant, the combination of the passage of the sterilant and the stirring being sufficient to maintain the powder in a fluidized state, and wherein the amount of sterilant employed is less than that required to fluidize the powder in the absence of stirring, the total energy required to pass the sterilant through the powder and to stir the powder is less than that required if fluidization is carried out utilizing the sterilant alone or stirring alone, and greater than one third of the vessel is initially filled with said powder.

2. A method according to claim 1 in which the vessel is evacuated before introducing the sterilant.

3. A method according to claim 1 in which the powder to be sterilized is talc.

* * * * *